(12) United States Patent
Tkaczyk et al.

(10) Patent No.: US 7,606,346 B2
(45) Date of Patent: Oct. 20, 2009

(54) CT DETECTOR MODULE CONSTRUCTION

(75) Inventors: John Eric Tkaczyk, Delanson, NY (US); Jonathan D. Short, Saratoga Springs, NY (US); Yanfeng Du, Rexford, NY (US); James Wilson Rose, Guilderland, NY (US); Charles G. Woychik, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 43 days.

(21) Appl. No.: 11/619,990

(22) Filed: Jan. 4, 2007

(65) Prior Publication Data
US 2008/0165921 A1 Jul. 10, 2008

(51) Int. Cl.
H05G 1/64 (2006.01)
G01T 1/20 (2006.01)
G01T 1/24 (2006.01)

(52) U.S. Cl. ............... 378/19; 378/98.8; 250/370.09
(58) Field of Classification Search .............. 378/19, 378/98.8; 250/370.09
See application file for complete search history.

(56) References Cited

U.S. PATENT DOCUMENTS

| | | | |
|---|---|---|---|
| 5,920,070 A * | 7/1999 | Petrick et al. ......... 250/370.09 |
| 6,396,898 B1 * | 5/2002 | Saito et al. ................. 378/19 |
| 6,510,195 B1 * | 1/2003 | Chappo et al. ............. 378/19 |
| 6,522,715 B2 * | 2/2003 | Hoffman et al. ........... 378/19 |
| 6,587,538 B2 * | 7/2003 | Igarashi et al. ............ 378/19 |
| 6,621,084 B1 * | 9/2003 | Wainer et al. ......... 250/370.09 |
| 6,658,082 B2 * | 12/2003 | Okumura et al. .......... 378/19 |
| 6,671,345 B2 * | 12/2003 | Vrettos et al. ............. 378/19 |
| 6,694,172 B1 * | 2/2004 | Gagnon et al. ............ 600/436 |
| 6,917,664 B2 * | 7/2005 | Chappo et al. ............. 378/19 |
| 6,990,176 B2 * | 1/2006 | Sherman et al. .......... 378/98.8 |
| 7,010,091 B2 * | 3/2006 | Hayashida et al. ....... 378/98.8 |
| 7,075,091 B2 * | 7/2006 | Hoffman ............. 250/370.11 |
| 7,189,971 B2 * | 3/2007 | Spartiotis et al. ...... 250/370.09 |
| 7,202,482 B2 * | 4/2007 | Yokoi et al. .......... 250/370.09 |
| 2005/0286682 A1 | 12/2005 | Tkaczyk et al. |

* cited by examiner

Primary Examiner—Allen C. Ho
(74) Attorney, Agent, or Firm—Jason K. Klindtworth

(57) ABSTRACT

A detector module for a CT imaging system is provided. The detector module includes a sensor element to convert x-rays to electrical signals. The sensor element is coupled to a data acquisition system (DAS) via an interconnect system, the DAS comprised of an electronic substrate and an integrated circuit. The interconnect system couples the sensor element, electronic substrate, and integrated circuit by way of a contact pad interconnect together with a wire bond interconnect or an additional contact pad interconnect.

22 Claims, 9 Drawing Sheets

CT DETECTOR MODULE CONSTRUCTION

BACKGROUND OF THE INVENTION

The present invention is generally related to an electrical interface for a sensor element, and, more particularly, to an integrated circuit (IC) based electrical interface between the sensor element and a data acquisition system (DAS), as may be used as a modular tileable element in a large area detector for in a computed tomography (CT) system.

Radiographic imaging systems, such as X-ray and computed tomography (CT) have been employed for observing, in real time, interior aspects of an object. Typically, the imaging systems include an X-ray source that is configured to emit X-rays toward an object of interest, such as a patient or a piece of luggage. A detecting device, such as an array of radiation detectors, is positioned on the other side of the object and is configured to detect the X-rays transmitted through the object.

One known detector used in a computed tomography (CT) system includes an energy discriminating, direct conversion detector. When subjected to x-ray energy, a sensor element in the direct conversion detector converts this x-ray to energy to produce an analog electrical signal corresponding to an incident photon flux.

A data acquisition system (DAS) may acquire the analog signals from the direct conversion detector and convert these signals to digital signals for subsequent processing. Interface packages traditionally utilized between the detector and the DAS have not enabled achieving optimal signal integrity for the analog signals. One factor in this non-optimal signal quality is the interconnect paths between the sensor element and the DAS. Current detector modules make interconnections from the sensor readout surface to the DAS with an interconnect structure involving long length metal traces on flexible or rigid circuit board. As the density of sensor elements increases, the routing of interconnects between the DAS and sensor becomes more difficult. More layers of packaging are required to route the interconnects, thus causing increased capacitance and decreased reliability.

Accordingly, it is desirable to provide a system of interconnects that provides short, low capacitance interconnection of a sensor element to the DAS. Furthermore, it is desirable that the sensor and signal processing electronics are packaged in a tileable unit with two, three, or four sides that butt to form a sensor array that has relatively small gaps between the units.

BRIEF DESCRIPTION OF THE INVENTION

The present invention provides an apparatus with an improved interconnect construction that overcomes the aforementioned drawbacks. A plurality of wire bonds and bump bonds form short low capacitance interconnects between the sensor element and various components in a DAS.

According to one aspect of the present invention, a CT imaging system includes a gantry having a bore therethrough designed to receive a patient being translated through the bore, an x-ray source disposed in the gantry and configured to emit x-rays toward the patient, and a detector module disposed in the gantry to receive x-rays signals attenuated by the patient. The detector module further includes a sensor element to convert the x-ray signals to corresponding electrical signals, a data acquisition system (DAS) to condition the electrical signals that includes at least one integrated circuit on an electronic substrate, and an interconnect system to couple the sensor element, the at least one integrated circuit, and the electronic substrate, wherein the interconnect system includes a first contact pad interconnect and one of a wire bonds interconnect and a second contact pad interconnect.

In accordance with another aspect of the present invention, a detector module for use in a CT imaging system includes a direct conversion sensor configured to receive x-ray signals and convert the x-ray signals to corresponding analog signals and a data acquisition system (DAS) having a chip package and at least one electronic device mounted to the chip package, the electronic device configured to convert the analog signals to corresponding digital signals. The detector module also includes a first bond system interconnecting the direct conversion sensor to one of the chip package and the electronic device by way of a first bump bond array and a second bond system interconnecting the electronic device to the chip package, wherein the second bond system comprises one of a wire bond array and a second bump bond array.

In accordance with yet another aspect of the present invention, a method of constructing a detector module includes the steps of positioning an x-ray sensor to receive x-rays from an x-ray source and positioning a data acquisition system (DAS) behind the x-ray sensor as compared to the x-ray source to condition electrical signals, the DAS including an electronic substrate having at least one integrated circuit thereon. The method also includes the steps of coupling the x-ray sensor to the electronic substrate by way of a bump bond system and coupling the at least one integrated circuit to the electronic substrate by one of a wire bond system and a second bump bond system.

Various other features and advantages of the present invention will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE INVENTION

Figure 1:
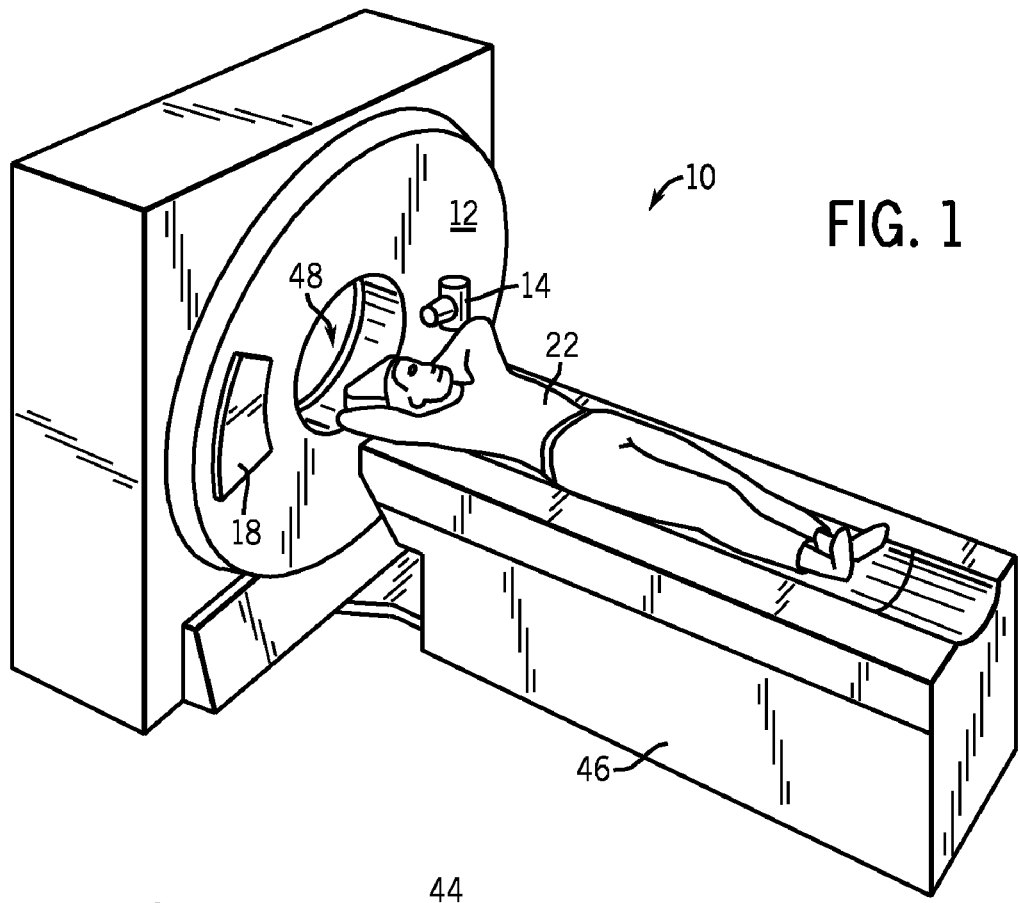
FIG. 1 is a perspective view of a computed tomography (CT) imaging system according to one embodiment of the present invention.
Figure 2:
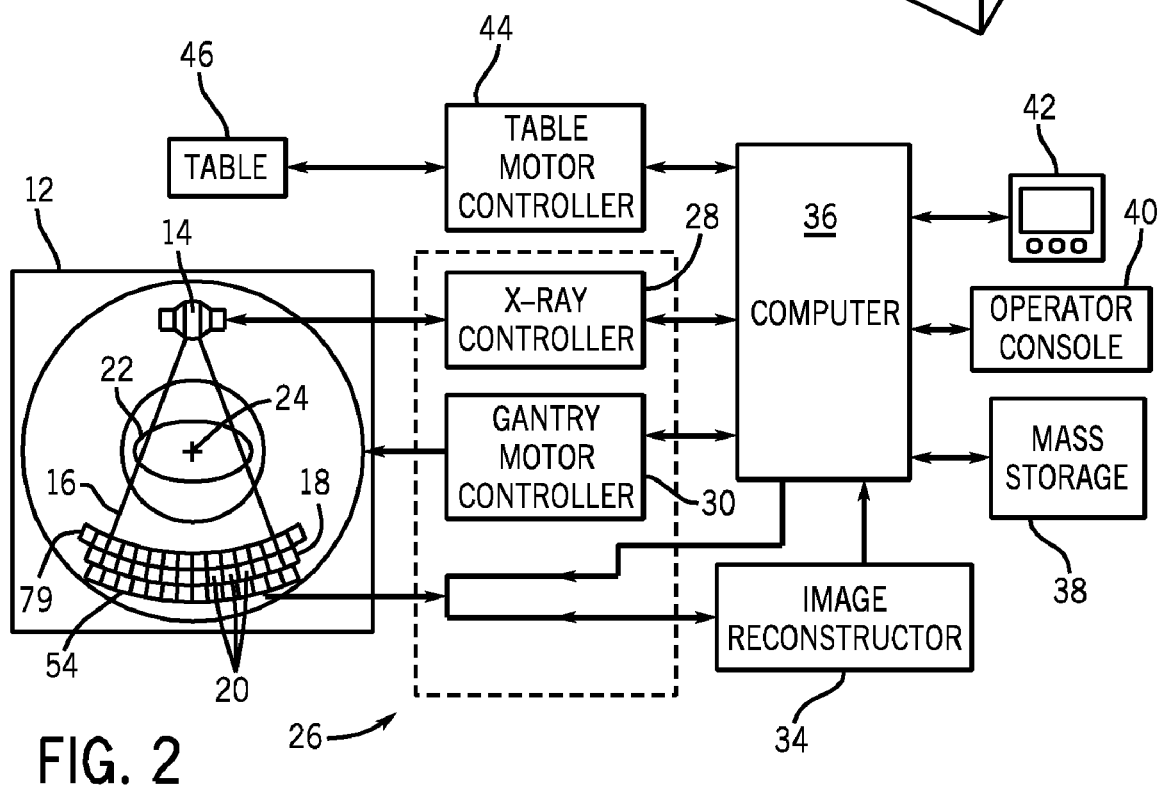
FIG. 2 is a schematic of the CT imaging system of FIG. 1.

Referring to FIGS. 1 and 2, an embodiment of a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. Detector assembly 18 is formed by a plurality of detector modules 20 which together sense the projected x-rays that pass through a medical patient 22. Each detector module 20 produces an electrical signal that represents not only the intensity of an impinging x-ray beam but is also capable of providing photon or x-ray count data, and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 54 and performs high speed reconstruction. The reconstructed image is applied as an input to a computer 36 which stores the image in a mass storage device 38.

Computer 36 also receives commands and scanning parameters from an operator via console 40 having a keyboard to input data parameters. An associated cathode ray tube display 42 allows the operator to observe the reconstructed image and other data from computer 36. The operator supplied commands and parameters are used by computer 36 to provide control signals and information to DAS 54, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48.

The detector modules 20 of CT imaging system 10 are constructed having an interface architecture that allows segregating (e.g., in an integrated circuit package) of signals having a given electrical characteristic (e.g., relatively sensitive analog signals) from signals having different electrical characteristics with respect to the given electrical characteristic (e.g., digital and/or power signals) by way of low capacitance interconnects. That is, the analog signals produced by an x-ray sensor in detector modules 20 are transmitted by way of interconnects to a data acquisition system (DAS) that provides a desired signal conditioning (e.g., analog-to-digital conversion) to the sensitive analog signals. Separate digital and power interconnects are disposed within the DAS that are segregated from the analog sensor interconnects to transmit digital signals and power. The DAS can include application specific integrated circuits created on silicon chips to provide dedicated functionality such as analog-to-digital conversion (ASIC). For example, the analog interconnections may be made at a first region of the ASIC chip (e.g., a top face of the ASIC chip), and the digital signals and power interconnections may be made at a second region spaced apart from the first region (e.g., adjacent sides of the ASIC or a bottom face of the ASIC). Typically the analog and digital connections to the ASIC are on one side of the silicon chip. It is contemplated that the exact combination and configuration of interconnects and their function will vary and is not limited to a specific detector module architecture. Rather, the embodiments described below are provided as exemplary configurations to carry out the present invention.

Figure 3:
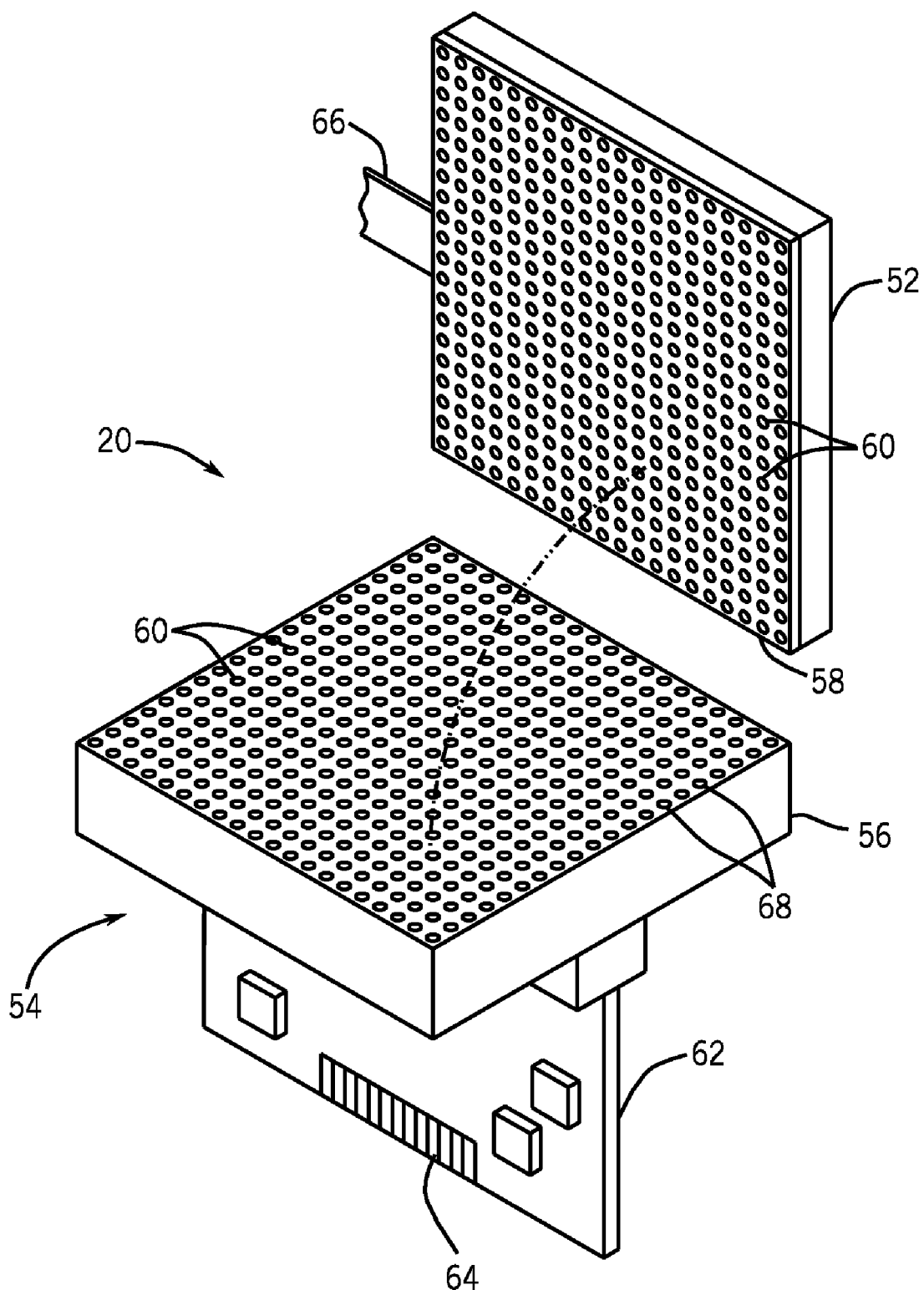
FIG. 3 is a perspective view of a detector module according to one embodiment of the present invention.

FIG. 3 shows a detector module 20 having construction features and assembly "stack-up" according to one embodiment of the present invention. The detector module 20 has the feature that it is tileable such that similar detector module units can be butted on all four sides. Detector module 20 includes a sensor element 52 configured to receive x-ray signals and convert the x-ray signals to corresponding electrical analog signals. Preferably, the sensor element 52 comprises a single layer of a direct conversion material, examples of which include cadmium telluride, cadmium zinc telluride crystals, polycrystalline compacts, and film layers. As shown in FIG. 3, sensor element 52 is coupled to DAS 54 to convert the analog signals to digital signals. Specifically, sensor element 52 is coupled to the electronic substrate 56 that forms part of DAS 54. To facilitate this coupling, a pitch adapter 58 is included between the sensor element 52 and the electronic substrate 56. The pitch adapter 58 is a double-sided connection having contact pads 60 on each surface thereof to join with contact pads 60 on the bottom readout surface of sensor element 52 and contact pads 60 on electronic substrate 56. The pitch adapter 58 is configured to join sensor element 52 to the electronic substrate 56 when different contact pad 60 configurations and/or pitches are present on the sensor element 52 and the electronic substrate 56. The top of the pitch adapter 58 has contact pads 60 corresponding to one contact pad configuration on the bottom side of the sensor element 52 and has bottom contact pads 60 corresponding to a different contact pad configuration on the electronic substrate 56.

It is also envisioned that the contact pads 60 of the sensor element 52 be in the same configuration as contact pads 60 on the electronic substrate 56. In this arrangement, a pitch adapter is not needed for coupling sensor element 52 to electronic substrate 56. In this configuration, sensor element 52 has a bottom readout surface having contact pads 60 thereon that are directly coupled to the electronic substrate 56. That is, the contact pads 60 on the bottom surface of sensor element 52 are arranged to couple with corresponding contact pads 60 on the top face of the electronic substrate 56.

The implementation of contact pads 60 as an interconnect between the sensor element 52 and the DAS 54 is particularly advantageous since it essentially allows a short connection (i.e., without interconnecting leads) with low capacitance between the sensor element 52 and the DAS 54. Preferably, the sensor element 52 includes an individual contact pad for each pixel in the direct conversion sensor. Such a configuration helps to ensure high quality transmission of the sensitive analog signals.

As shown in FIG. 3, electronic substrate 56 is also connected to or integrated with a routing assembly 62 oriented perpendicularly to the sensor element 52 and electronic substrate 56. The perpendicular orientation of routing assembly 62 allows for a connection to the digital interconnect 64 located thereon, thus allowing for improved transmission of digital data from detector module 20 to processing components of CT scanning system 10 of FIG. 1. In addition, electronic substrate 56 and routing assembly 62 have no components on their sidewalls that extend beyond the sensor element 52 in order to allow each side of the sensor element 52 to butt closely to another detector module of the same type. In this way, four-sided tileablility is provided by this design and facilitates the construction of large area detectors.

Detector module 20 also includes a high voltage interconnect 66 which makes contact with sensor element 52 at a common cathode thereof to provide power to the detector module 20. It is anticipated that this connection 66 can be common to many detector modules 20 and applied after detector modules 20 are tiled into a large array. The high voltage interconnect 66 is insulated to prevent shorting to other parts of the detector module 20 other than the cathode contact. A bias voltage control 68 is also included in detector module 20 and form additional connections separate from the pixel anode connections. The bias voltage control 68 connects between the sensor element 52 or pitch adapter 58 to DAS 54. In the embodiment shown in FIG. 3, bias voltage control 68 is in the form of a contact pad 60 and is integrated into the overall contact pad 60 interconnect. It is also envisioned that bias voltage control 68 could be made through a separate wire bond or voltage line. The number of bias voltage controls 68 employed connecting the sensor element 52 to the DAS 54 will vary depending on the values of the expected incident flux rate of x-ray photons received by the sensor element 52. The function of the bias voltage control 68 is to adjust active area of the sensor element 52 dynamically depending on the x-ray photon flux rate to prevent saturation of the sensor element 52. The active area of the sensor element 52 or the degree of sub-pixel element binning may be adjusted by controlling voltages through the bias voltage control 68.

Figure 4:
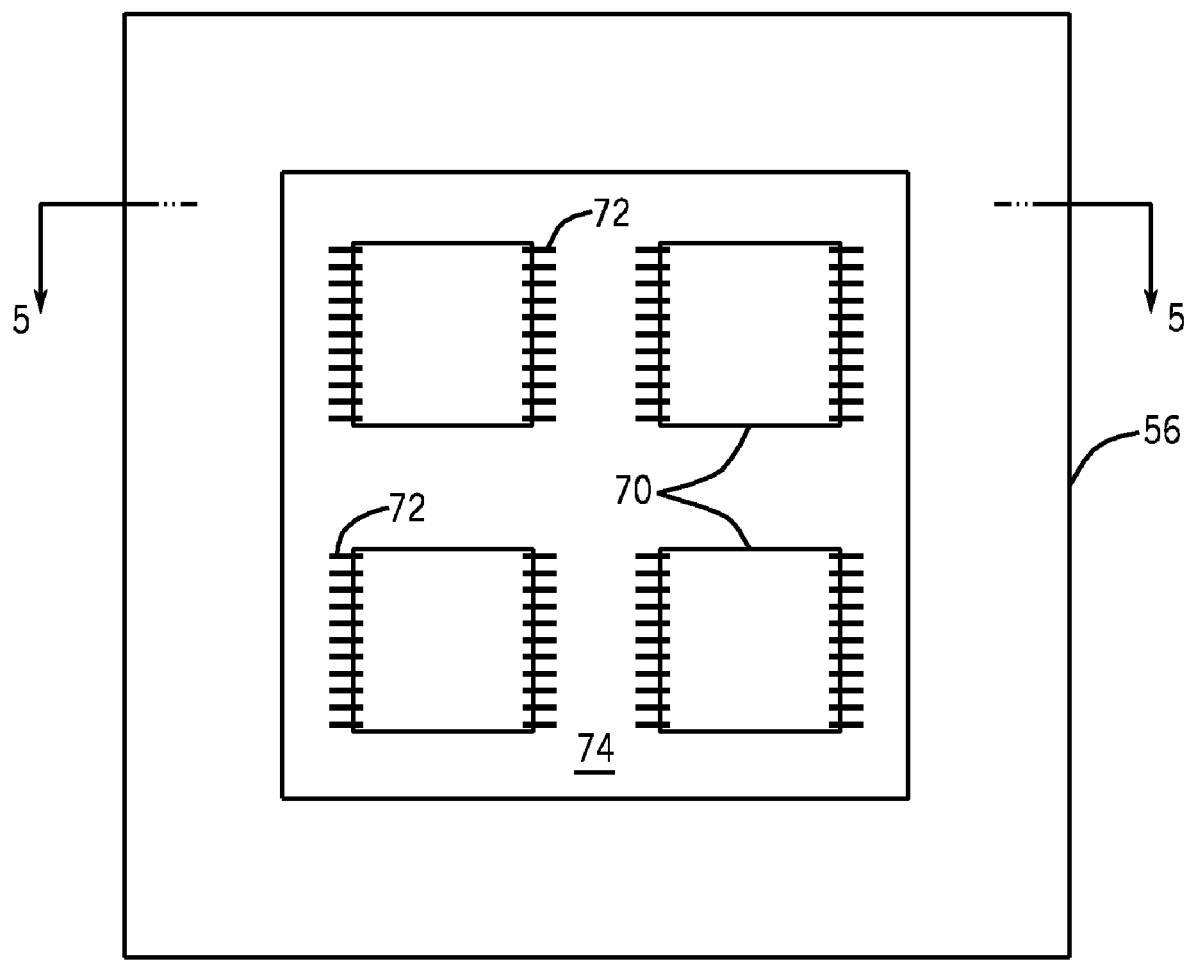
FIG. 4 is a bottom plan view of the detector module of FIG. 3.
Figure 5:
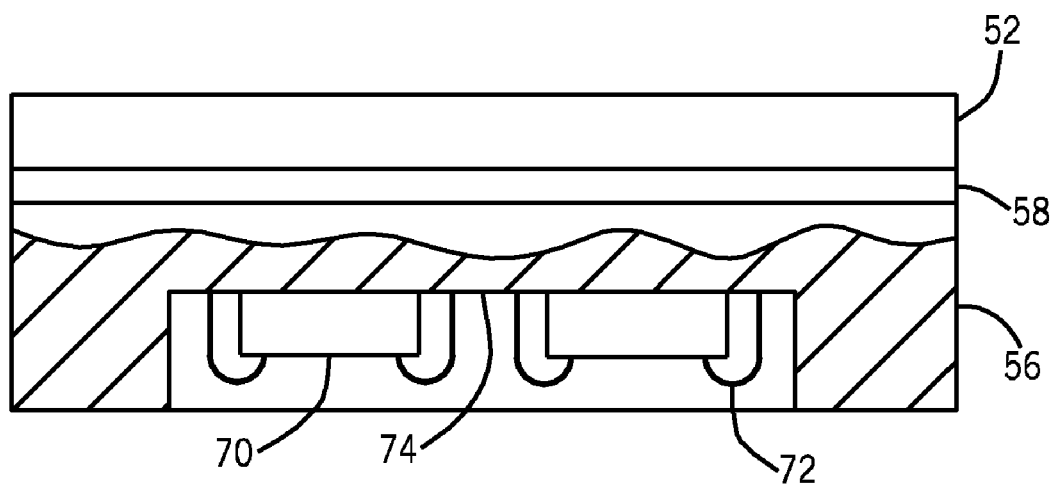
FIG. 5 is a side cross-sectional view taken along line 4-4 of FIG. 4.

As shown in FIGS. 4 and 5, DAS 54 also includes at least one integrated circuit 70 mounted to the bottom of electronic substrate 56. Other active and passive circuits including resistors and capacitors can also be present. Preferably, at least one integrated circuit 70 is configured as a photon counting application specific integrated circuit (ASIC) capable of converting the analog signal from the sensor element 52 to a digital signal. This ASIC, or other similar circuit, provide data or feedback as to the number and/or energy of photons detected in the x-rays received by sensor element 52. As is typical of integrated circuits fabricated by a conventional CMOS process, the interconnection pads for analog input, digital output, and power connections are formed on the top surface 76 of the integrated circuits 70, which is the same side as the processing circuits. Most conventional integrated circuits 70 are electrically connected to electronic substrate 56 by way of wire bonds 72 located on the periphery of the top surface 76 of the integrated circuits 70. Wire bonds 72 couple the integrated circuits 70 to electronic substrate 56 to transfer analog input received from sensor element 52 and to transfer digital signals and power signals. As shown in FIG. 5, the wire bonds 72 originate on the top surface 76 of the integrated circuit 70 and route across the thickness of the integrated circuit 70 to the backside surface of the DAS substrate 74. Alternately, a flip chip mounting of the ASIC uses an area array configuration of contact pads to couple the signals without wirebonds. For the flip chip configuration, the top surface 76 of the integrated circuits 70 is facing toward the surface 74 of the electrical substrate 56. It is not envisioned that some combination of wire bonds and flip chip can be accommodated on this package shown in FIGS. 4 and 5, but this will be addressed by embodiments shown in later figures.

As shown in FIGS. 4 & 5, wire bonds 72 are positioned on a bottom surface 74 of electronic substrate 56 in connection with the integrated circuits 70. The wire bonds serve to provide all analog, digital and power connections. Wire bonds 72 are positioned to have a detailed layout such as to physically separate analog and digital interconnect traces and layers. In addition, ground shielding traces and layers will be integrated into the design of the electronic substrate 56 such that they are physically positioned between or adjacent to the analog and digital lines. In this way, the interference between analog and digital signals are avoided on the wire bonds 72 and on the coupling of the sensor element 52 to electronic substrate 56 by way of contact pads 60, as shown in FIG. 3. As such, signal integrity of the analog signals can be maintained during transmission between the sensor element 52 and the DAS 54.

Figure 6:
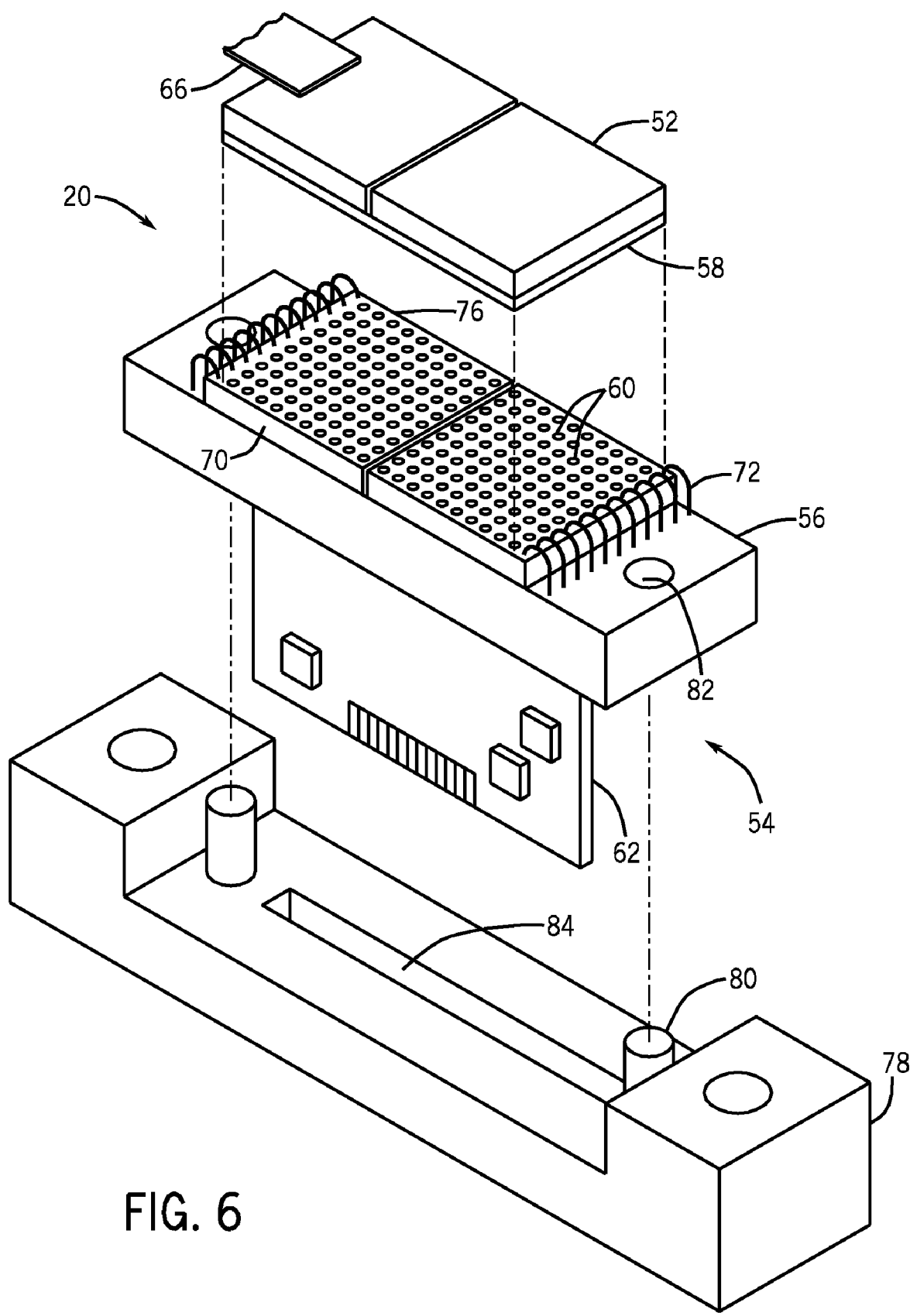
FIG. 6 is an exploded perspective view of a detector module according to another embodiment of the present invention.

An additional embodiment of detector module 20 is shown in FIG. 6 that can accommodate the case where the integrated circuit 70 has both flip chip and wire bond pads. The combination of flip chip and wire bonds may provide improved isolation of analog and digital signals. As illustrated therein, the integrated circuits 70 (i.e., ASICs) are mounted to the top of electronic substrate 56. In this embodiment, contact pads 60 on top surface 76 of integrated circuits 70 provide analog connections between sensor element 52 and the integrated circuits 70. Digital signal connections and power connections are formed by wire bonds 72 connected to top surface 76 of integrated circuits 70 and running to electronic substrate 56. Wire bonds 72 are positioned at opposing ends of the integrated circuits 70 and adjacent to the contact pads 60 interconnect so as not to interfere with the coupling of the sensor element 52 to the integrated circuits 70.

Also shown in FIG. 6 is module support 78 that aligns detector module 20 in the overall detector assembly 18 and collimator assembly 79 shown in FIG. 2. Detector module 20 is secured to module support 78 by inserting alignment pins 80 of module support 78 into apertures 82 on the electronic substrate 56, although it is envisioned that other connection mechanisms can connect detector module 20 to module support 78. Alignment pins 80 properly position detector assembly 20 with collimator assembly 79 of FIG. 2 so that x-ray beams are collimated before impinging upon sensor element 52. Also formed in module support 78 is slot 84 that allows the perpendicularly aligned routing assembly 62 to pass therethrough.

Figure 7:
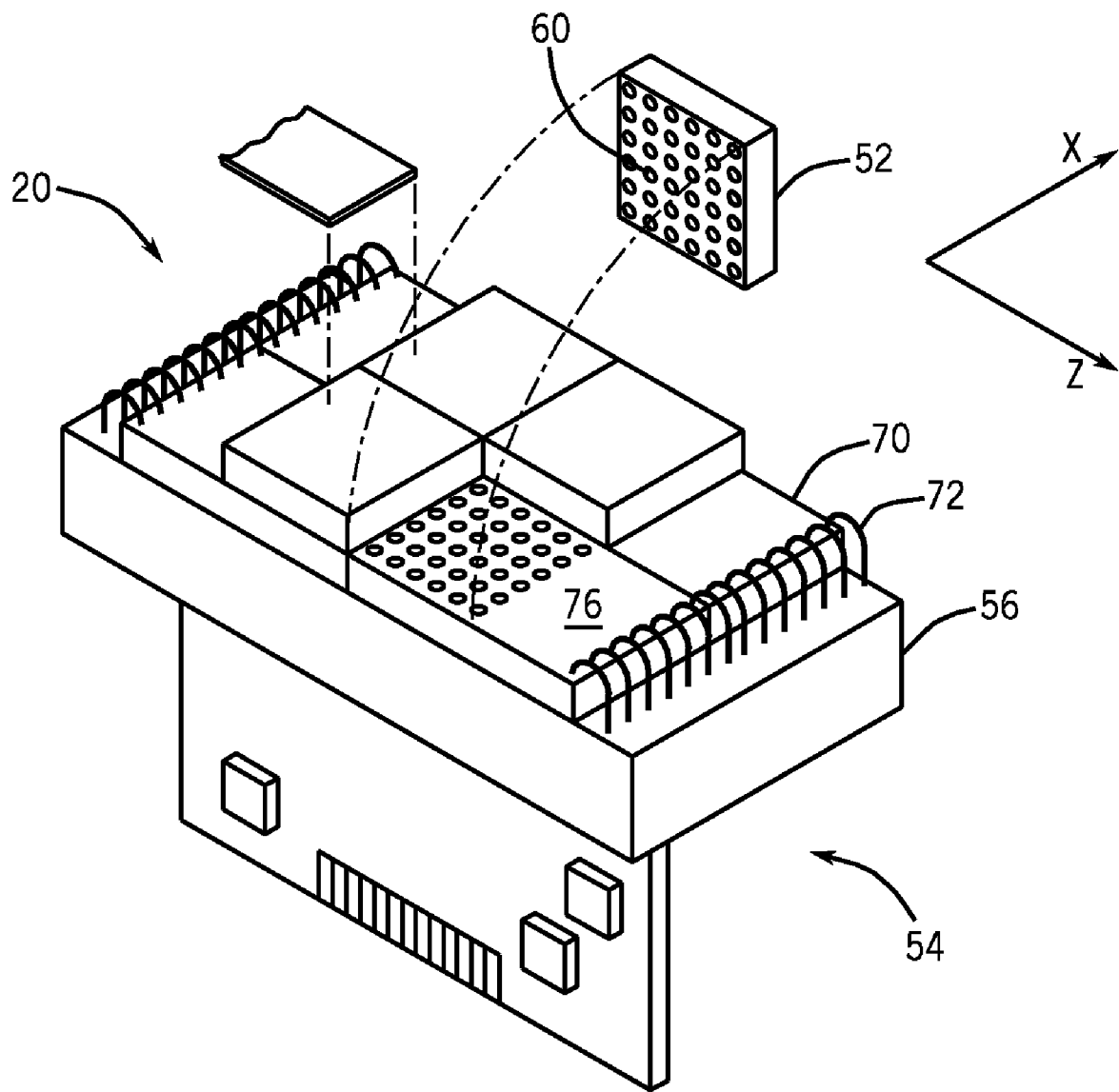
FIG. 7 is a partially exploded perspective view of a detector module according to another embodiment of the present invention.

FIG. 7 shows an additional embodiment of detector module 20 in which the integrated circuits 70 are mounted on top of electronic substrate 56. In this embodiment, contact 60 pads on top surface 76 of integrated circuits 70 provide analog connections between sensor element 52 and the integrated circuits 70. Digital signal connections and power connections are formed by wire bonds 72 connected to top surface of integrated circuits 70 and running to electronic substrate 56. Wire bonds 72 are positioned at opposing ends of the integrated circuits 70 and adjacent to the contact pads 60 interconnect so as not to interfere with the coupling of the sensor element 52 to the integrated circuits 70. As shown in FIG. 7, each integrated circuit 70 is configured to be three side buttable with additional integrated circuits 70. This allows a width along the z-axis of two integrated circuits 70 and a length along the x-axis that is unconstrained as to the number of integrated circuits 70. This construction allows for a greater density of sensor elements 52 to be coupled to the integrated circuits 70.

Figure 8:
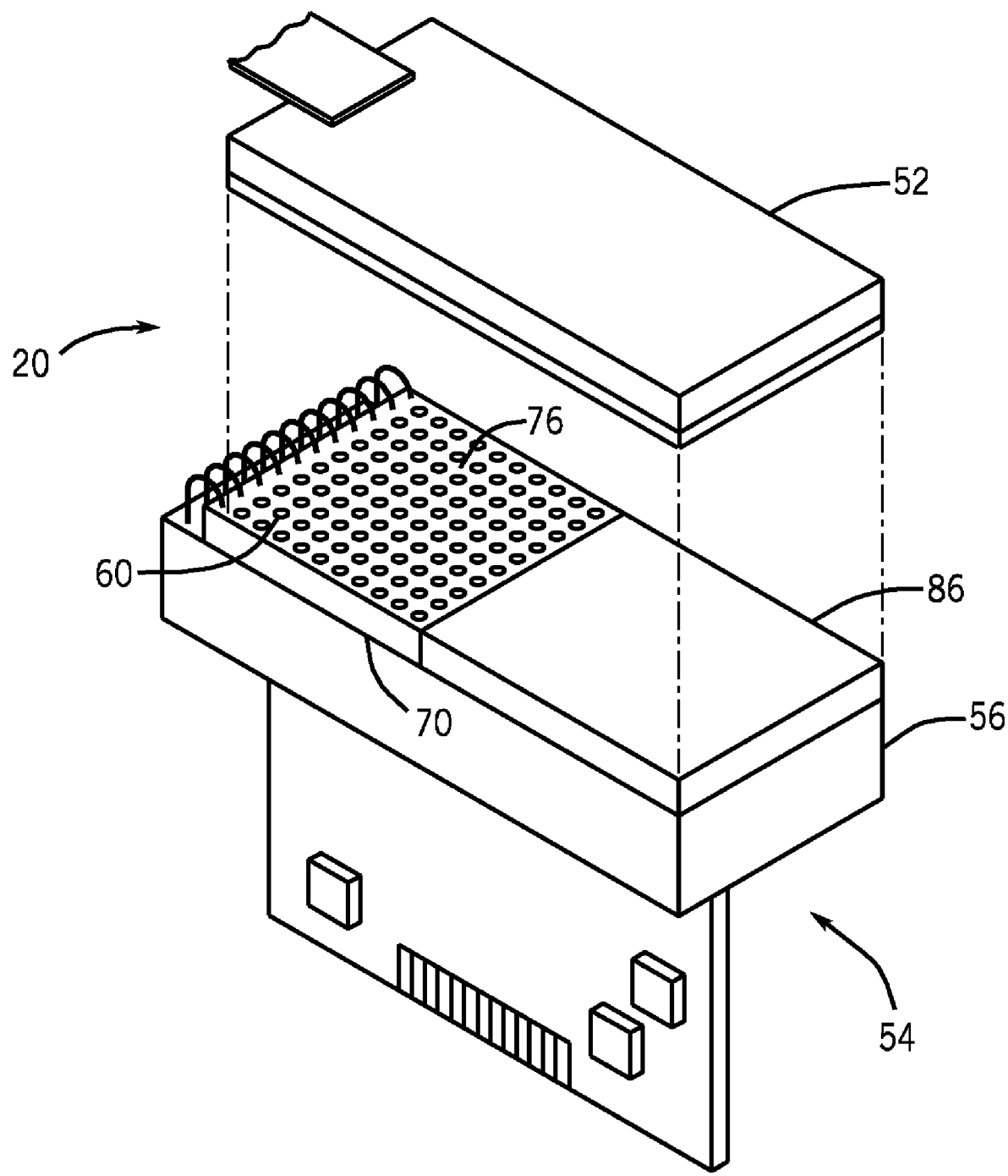
FIG. 8 is a partially exploded perspective view of a detector module according to another embodiment of the present invention.

In the embodiment of FIG. 8, contact pads 60 on top surface 76 of integrated circuit 70 provide analog connections between sensor element 52 and the integrated circuit 70. The area of sensor element 52 is larger than that of integrated circuit 70, and as such, a portion of sensor element 52 overhangs integrated circuit 70. To provide support for sensor element 52, insulating support member 86 is positioned between the overhanging portion of sensor element 52 and electronic substrate 56 in order to make the detector module 20 more mechanically robust.

Figure 9:
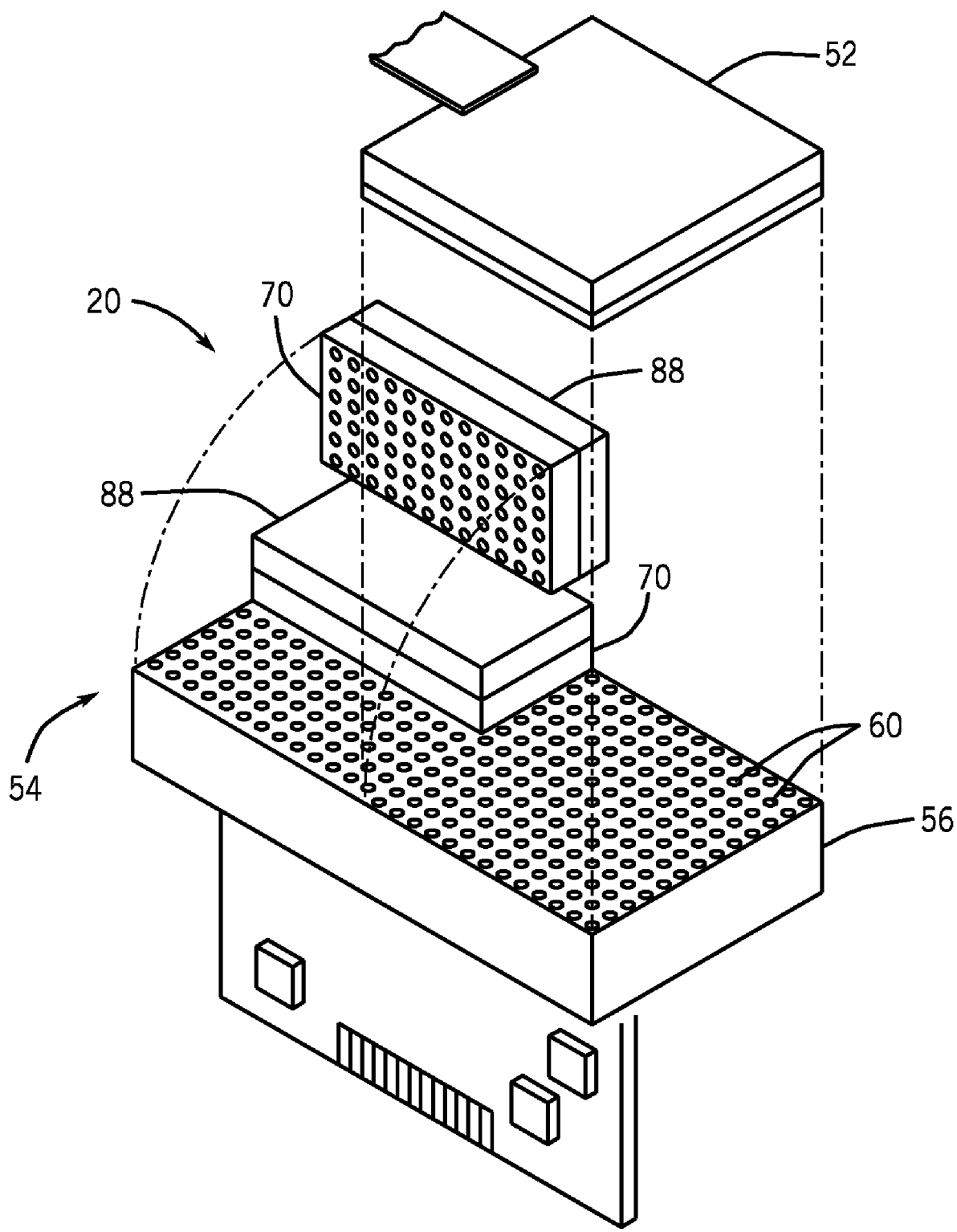
FIG. 9 is a partially exploded perspective view of a detector module according to another embodiment of the present invention.

In the embodiment of FIG. 9, sensor element 52 and integrated circuits 70 are positioned in a side-by-side configuration. Both the sensor element 52 and the integrated circuits 70 are connected to electronic substrate 56 by way of contact pads 60, which transmit the analog signals, digital signals, and the power signals. In this configuration, radiation shield 88 is positioned above integrated circuit 70 to shield the integrated circuit 70 from x-ray exposure. The radiation shield 88 is comprised of a slug made of tungsten or any other suitable metal or alloy, positioned to block X-rays that otherwise could impinge onto the integrated circuit 70.

Figure 10:
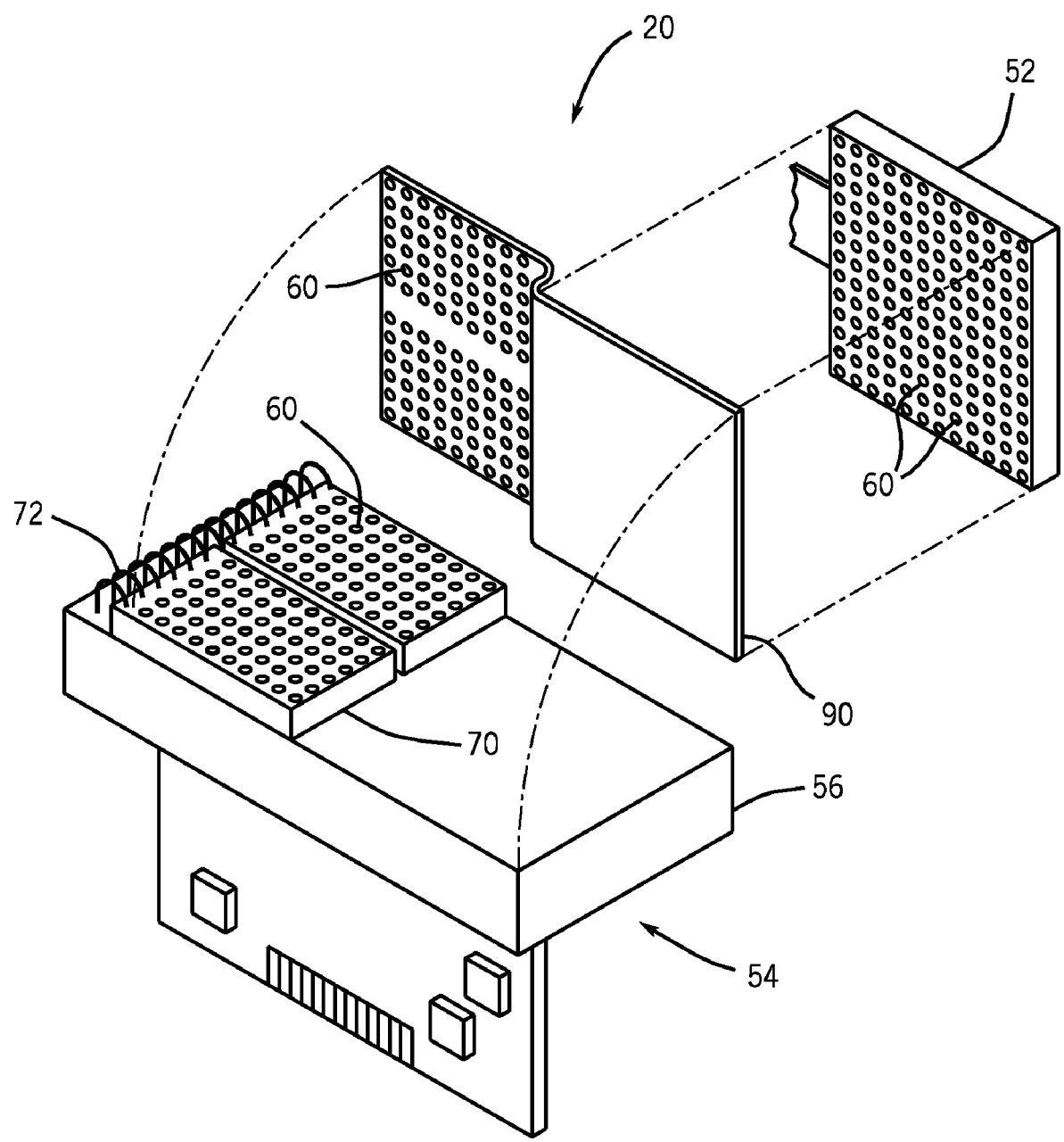
FIG. 10 is a partially exploded perspective view of a detector module according to another embodiment of the present invention.

In an alternate embodiment, and as shown in FIG. 10, when sensor element 52 and integrated circuit 70 are in a side-by-side configuration and wire bonds 72 are used to connect the integrated circuit 70 to electronic substrate 56, a flexible pitch adapter 90 is included to interconnect the sensor element 52 to integrated circuit 70. Flexible pitch adapter 90 provides a contact pad interconnect 60 between the sensor element 52 and the integrated circuit 70 to transmit analog signals therebetween. Wire bonds 72 are positioned adjacent to the contact pad interconnect 60 to connect integrated circuit 70 to electronic substrate 56 to transmit digital data and power.

Figure 11:
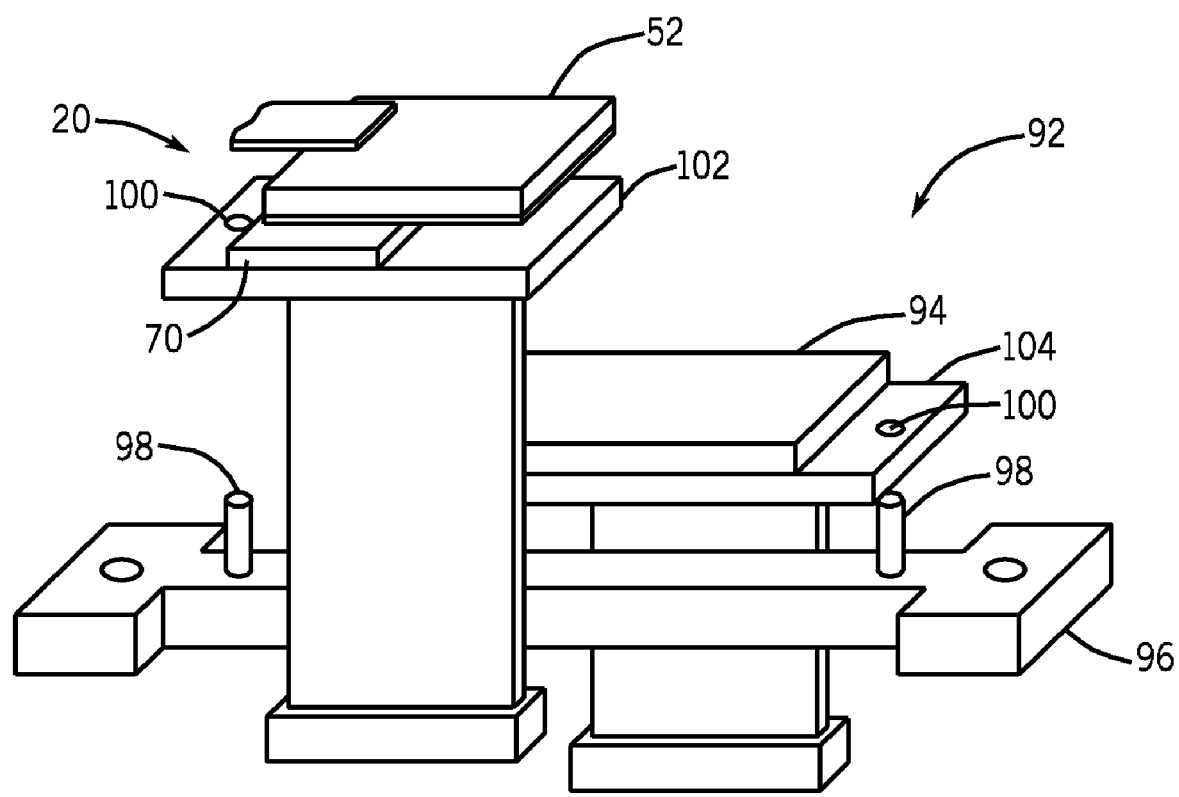
FIG. 11 is a perspective view of a detector module according to another embodiment of the present invention.

It is also envisioned that detector module 20 forms part of a layered hybrid detector 92 as shown in FIG. 11. The exact construction of detector module 20 included in layered hybrid detector 92 can vary according to any of the previous embodiments described above and will not be set forth in detail here. The layered hybrid detector 92 also includes a scintillator array 94 positioned behind the detector module 20 that includes the direct conversion sensor 52. In a preferred embodiment, the direct conversion sensor 52 is composed of a thin layer of direct conversion material of approximately 0.2 mm in thickness and the scintillator array 94 is composed of a scintillating material of a greater thickness of approximately 3 mm. The construction of the layered hybrid detector 92, which includes direct conversion sensor 52 and scintillator array 94, allows for reception and transmission of both low and high energy x-rays and improved data collection over a wide range of input x-ray flux rates.

As shown in FIG. 11, the layered hybrid detector 92 is constructed to align with a module support 96 by inserting alignment pins 98 of module support 96 into apertures 100 on the electronic substrates 102, 104 on which direct conversion sensor 52 and scintillator array 94 are mounted respectively. Alignment pins 98 properly position layered hybrid detector 92 with collimator assembly 79 of FIG. 2 so that x-ray beams are collimated before such beams impinge upon the direct conversion sensor 52 and scintillator array 94. It is also envisioned that other similar connection mechanisms can connect layered hybrid detector 92 to module support 96.

It is contemplated that the described electrical interface architectures and interconnect systems will enable a detector module that in one example application, such as in a multi-slice CT system, provides the following exemplary advantages: reduction of unwanted signal current, capacitance, and/or inductance to increase sensor element signal integrity, relatively uncomplicated manufacturing and serviceability, reduced cost, and improved reliability through reduction of number and/or length of interconnects.

Therefore, according to one embodiment of the present invention, a CT imaging system includes a gantry having a bore therethrough designed to receive a patient being translated through the bore, an x-ray source disposed in the gantry and configured to emit x-rays toward the patient, and a detector module disposed in the gantry to receive x-rays signals attenuated by the patient. The detector module further includes a sensor element to convert the x-ray signals to corresponding electrical signals, a data acquisition system (DAS) to condition the electrical signals that includes at least one integrated circuit on an electronic substrate, and an interconnect system to couple the sensor element, the at least one integrated circuit, and the electronic substrate, wherein the interconnect system includes a first contact pad interconnect and one of a wire bonds interconnect and a second contact pad interconnect.

In accordance with another embodiment of the present invention, a detector module for use in a CT imaging system includes a direct conversion sensor configured to receive x-ray signals and convert the x-ray signals to corresponding analog signals and a data acquisition system (DAS) having a chip package and at least one electronic device mounted to the chip package, the electronic device configured to convert the analog signals to corresponding digital signals. The detector module also includes a first bond system interconnecting the direct conversion sensor to one of the chip package and the electronic device by way of a first bump bond array and a second bond system interconnecting the electronic device to the chip package, wherein the second bond system comprises one of a wire bond array and a second bump bond array.

The present invention has been described in terms of the preferred embodiment, and it is recognized that equivalents, alternatives, and modifications, aside from those expressly stated, are possible and within the scope of the appending claims.

What is claimed is:

1. A CT imaging system comprising:
   a gantry having a bore therethrough designed to receive a patient being translated through the bore;
   an x-ray source disposed in the gantry and configured to emit x-rays toward the patient; and
   a detector module disposed in the gantry to receive x-rays signals attenuated by the patient, wherein the detector module further comprises:
   a sensor element to convert the x-ray signals to corresponding electrical signals;
   at least one bias voltage control connected to the sensor element to provide functionality to dynamically control a sensor pixel configuration in the detector module;
   a data acquisition system (DAS) to condition the electrical signals, the DAS comprising at least one integrated circuit on an electronic substrate, the DAS further connected to the at least one bias voltage control; and
   an interconnect system to couple the sensor element, the at least one integrated circuit, and the electronic substrate, wherein the interconnect system includes a first contact pad interconnect and one of a wire bonds interconnect and a second contact pad interconnect.

2. The CT imaging system of claim 1 wherein the interconnect system forms an analog connection, a digital connection, and a power connection between the sensor element, the at least one integrated circuit, and the electronic substrate.

3. The CT imaging system of claim 2 wherein the analog connection, the digital connection, and the power connection are electrically and physically segregated and electrically shielded.

4. The CT imaging system of claim 1 wherein the detector module further comprises a pitch adapter, the pitch adapter including:
   a top surface having a plurality of contact pads thereon to interconnect to a readout surface of the sensor element; and
   a bottom surface having a plurality of contact pads thereon to interconnect to one of the electronic substrate and the at least one integrated circuit.

5. The CT imaging system of claim 1 wherein the detector module further comprises an electrical routing assembly connected to the electronic substrate, the electrical routing assembly oriented perpendicular to the sensor element, the electronic substrate and the electrical routing assembly having no components on respective sidewalls that extend beyond the sensor element, to form a four-side buttable detector module whereby additional detector modules can be positioned adjacent thereto to construct a larger area sensor array.

6. The CT imaging system of claim 1 further comprising a collimator assembly, wherein the detector module further includes a module support attached to the electronic substrate to align the sensor element with the collimator assembly.

7. The CT imaging system of claim 1 wherein the detector module further comprises a high voltage interconnect coupled to the sensor element.

8. The CT imaging system of claim 1 wherein the at least one integrated circuit is configured to be three-side buttable to additional integrated circuits.

9. The CT imaging system of claim 1 wherein the detector module further comprises an insulating support layer configured to mechanically support an overhang region of the sensor element.

10. The CT imaging system of claim 1 wherein the sensor element and the at least one integrated circuit are positioned in a side-by-side arrangement on the electronic substrate.

11. The CT imaging system of claim 1 wherein the detector module further comprises a scintillator positioned behind the sensor element as compared to the x-ray source to receive x-rays attenuated by the patient.

12. The CT imaging system of claim 11 wherein the scintillator is configured to have a thickness greater than the sensor element and wherein the thickness of the scintillator prevents passage of a majority of the x-rays therethrough.

13. The CT imaging system of claim 1 wherein the integrated circuit is a photon counting application specific integrated circuit (ASIC).

14. The CT imaging system of claim 1 wherein the sensor element is a direct conversion sensor composed of one of cadmium telluride, cadmium zinc telluride crystals, and polycrystalline compacts.

15. A detector module for use in a CT imaging system, the detector module comprising:
  a direct conversion sensor configured to receive x-ray signals and convert the x-ray signals to corresponding analog signals;
  at least one bias voltage control for dynamic adjustment of an active area of a sensor element in the detector module;
  a data acquisition system (DAS) having an integrated circuit mounted to an electronic substrate, the integrated circuit configured to convert the analog signals to corresponding digital signals, the DAS further connected to the at least one bias voltage control;
  a first bond system interconnecting the direct conversion sensor to one of the integrated circuit and the electronic substrate, wherein the first bond system comprises a first bump bond array; and
  a second bond system interconnecting the integrated circuit to the electronic substrate, wherein the second bond system comprises one of a wire bond array and a second bump bond array.

16. The detector module of claim 15 wherein the second bond system is positioned apart from the first bond system so as not to interfere therewith.

17. The detector module of claim 15 wherein the detector module further comprises a pitch adapter configured to connect a first bump bonds pitch on the direct conversion sensor to a second bump bonds pitch on one of the integrated circuit and the electronic substrate.

18. The detector module of claim 15 wherein the integrated circuit is integrated with a routing assembly oriented perpendicular to the direct conversion sensor to form a four sided detector module whereby additional detector modules can be combined on all four sides to construct a larger area sensor array.

19. The detector module of claim 15 wherein the detector module further comprises a module support configured to attach to the integrated circuit and align the direct conversion sensor with a collimator assembly.

20. The detector module of claim 15 further comprising a scintillator array positioned behind the direct conversion sensor to receive x-ray signals passing through the direct conversion sensor.

21. A method of constructing a detector module comprising the steps of:
  positioning an x-ray sensor to receive x-rays from an x-ray source;
  positioning a scintillator behind the x-ray sensor as compared to the x-ray source to receive x-rays from the x-ray source;
  positioning a data acquisition system (DAS) behind the x-ray sensor as compared to the x-ray source, the DAS including an electronic substrate having at least one integrated circuit thereon;
  coupling the x-ray sensor to the electronic substrate by way of a bump bond system; and
  coupling the at least one integrated circuit to the electronic substrate by one of a wire bond system and a second bump bond system.

22. The method of claim 21 further including the step of imposing a pitch adapter between a first bump bond configuration on the x-ray sensor and a second bump bond configuration on the DAS.

* * * * *